(12) United States Patent
Putman et al.

(10) Patent No.: US 6,829,951 B2
(45) Date of Patent: Dec. 14, 2004

(54) PROCESS FOR THE PHYSICAL TESTING OF RUBBER

(75) Inventors: John B. Putman, Cuyahoga Falls, OH (US); Matthew C. Putman, Cuyahoga Falls, OH (US)

(73) Assignee: Tech Pro, Inc., Cuyahoga Falls, OH (US)

( * ) Notice: Subject to any disclaimer, the term of this patent is extended or adjusted under 35 U.S.C. 154(b) by 21 days.

(21) Appl. No.: 10/403,590

(22) Filed: Apr. 1, 2003

(65) Prior Publication Data

US 2004/0194555 A1 Oct. 7, 2004

(51) Int. Cl.[7] .............................................. G01N 11/10
(52) U.S. Cl. ............................................... 73/862.321
(58) Field of Search ...................... 73/861.321, 861.322, 73/54.27, 54.28, 54.39

(56) References Cited

U.S. PATENT DOCUMENTS 4,546,438 A * 10/1985 Prewitt et al. ................. 73/815
5,495,772 A * 3/1996 Dinzburg et al. ........... 73/865.8

* cited by examiner

Primary Examiner—Edward Lefkowitz
Assistant Examiner—T Miller
(74) Attorney, Agent, or Firm—Renner, Kenner, Greive, Bobak, Taylor & Weber

(57) ABSTRACT

A process for testing the properties of a rubber sample is provided. This process is suitable for use with current rheometers, curemeters, viscometers, and the like, wherein it is common to change test conditions during the duration of the test, when the rubber sample scorches or reaches full cure. This process provides a method for determining an optimal time for changing the test conditions to which the rubber sample is subjected. With this process specifying times for changing test conditions is no longer required prior to starting the test. Rather, the variable test condition is changed at sample-specific times that closely coincide with the actual scorch time or full cure time of the sample.

12 Claims, 1 Drawing Sheet

PROCESS FOR THE PHYSICAL TESTING OF RUBBER

BACKGROUND OF THE INVENTION

The present invention generally relates to the physical testing of rubber compounds. More particularly, the present invention relates to a process for physically testing a rubber sample, in real time, by continuously measuring the state of cure of the rubber sample and making adjustments to a test variable based upon the measured state of cure.

The physical testing of rubber compounds typically involves the measuring of tension, compression or shear. The measured parameters are generally either a resultant stress caused by an applied strain or a resultant strain caused by an applied stress. These tests seek to provide processability and vulcanization properties of a rubber sample. Processability, as defined by ASTM D1566, is "the relative ease with which raw or compounded rubber can be handled in rubber machinery." Thus, a rubber can be processed when it is able to be mixed, formed and shaped, and, thus, in order to be processed, a rubber must be capable of flow. Vulcanization, as defined by ASTM D1566, is "an irreversible process during which a rubber compound, through a change in its chemical structure (for example, cross linking), becomes less plastic. Thus, processability tests measure rubber properties while the rubber sample is still plastic and able to flow, and vulcanization tests measure rubber properties as the rubber sample changes from a plastic state to a more rigid state.

The rubber samples tested typically contain vulcanizing agents. Thus, the rubber samples will vulcanize to some degree during testing, and may purposefully be caused to vulcanize during testing, such that both processability and vulcanization characteristics may be analyzed in a single test, using appropriate equipment and test conditions. Particularly, the vulcanizing agents within the rubber sample will cause it to vulcanize during the test, and the vulcanization of the sample may be accelerated by increasing the temperature of the sample. Upon completion of vulcanization (i.e., full cure), the temperature of the rubber sample may be decreased and the after cure properties of the rubber may be analyzed. ASTM D6601 addresses the concept of curing a vulcanizable material at an elevated temperature, and subsequently reducing the temperature to measure after-cure properties. Thus, effective test equipment and methods measure processability characteristics of a rubber sample while it is able to flow, measure vulcanization characteristics of the rubber sample from scorch to full cure, and thereafter measure after-cure characteristics of the rubber sample.

Many instruments have been devised to test rubber samples in order to quantify processability and vulcanization properties of the rubber. Devices of the prior art include plastometers, curemeters, viscometers and rheometers, such as those disclosed in U.S. Pat. Nos. 2,037,529; 3,182,494; 3,479,858; 3,488,992; 3,494,172; 3,688,568; 4,829,830; 4,953,406; and 5,526,693, all of which are incorporated herein by reference. The earlier prior art devices were generally operated at isothermal conditions. It was realized that isothermal conditions did not simulate actual factory conditions, and U.S. Pat. No. 3,531,996, incorporated herein by reference, taught a method for testing the rubber sample at variable temperatures specified by a predetermined time/temperature profile, and, it is now common practice in the art to employ such time/temperature profiles. Thus, present day equipment and methods, as mentioned above, offer the ability to ramp temperatures from one given temperature to another given temperature at a specified time, and non-limiting examples of these, all incorporated by reference, are reported by John Sezna, Paper #173, presented to the Rubber Division, ASC, Orlando, Fla. 1999; John Sezna, Paper presented to the Northeast Ohio Rubber Group, Apr. 17, 2001; H. G. Burhin, Rubber Technology International, pp. 41–43 (1997); and DIN 53 529, Part II, Deutsches Institute fur Normung (1983).

It has also been found to be beneficial in measuring processability, vulcanization and after-cure characteristics to vary test parameters other than temperature. For instance, ASTM D6204 suggests measuring flow properties according to (1) a frequency sweep in which the frequency is programmed to change in steps under constant strain, amplitude and temperature; (2) a strain sweep in which the strain amplitude is programmed to change in steps under constant frequency and temperature conditions; and (3) a temperature sweep in which the temperature is programmed to either increase or decrease under constant strain, amplitude and frequency. U.S. Pat. No. 4,552,025, incorporated herein by reference, also describes that it is desirable to measure the viscoelastic properties of a rubber sample at one or more frequencies and temperatures, in order to better quantify the material's processability.

From the above, it can be seen that the processes and devices employed in determining rubber characteristics should be multifunctional, being capable of determining processability characteristics at one or more temperatures; vulcanization characteristics at the same or other temperatures; and after-cure properties at the same or other temperatures. Also, these various characteristics may be analyzed with variable conditions other than temperature, as mentioned above, wherein it was noted that the frequency or amplitude of an applied strain may be the variable condition. In addition, it is desirable that present methods and devices be capable of defining the physical properties of complex dynamic torque, elastic torque, viscous torque, complex dynamic modulus, elastic modulus, viscous modulus, and tangent delta, as defined in ASTM D5289, ASTM D6204, and ASTM D6601.

Processability characteristics testing takes place before the onset of vulcanization (i.e., before scorching of the rubber sample), vulcanization characteristics testing takes place from the time of scorching of the sample until full cure thereof, and after-cure characteristics testing takes place after full cure. The focus in the art is to either step or ramp change a test condition for one or more of these test periods. Currently, changing a test condition during rubber sample testing requires specifying test conditions prior to the start of the test, such that the variable test condition is step changed or ramped at a predetermined time that may or may not closely approximate the actual scorch time or full cure time. Because the times necessary for reaching scorch and full cure may vary from one rubber sample to another, researchers typically err on the side of making test times unnecessarily long in order to ensure that (1) all sample batches scorch before the condition is varied, in vulcanization testing, and (2) all sample batches are completely cured before the condition is varied, in after cure testing.

In general, a trial-and-error approach is employed to determine a time/variable condition profile (i.e., a profile of the time(s) at which the variable condition should be step changed or ramped) for vulcanization testing and/or after cure testing, in order for a set of rubber batches to be tested and compared. For example, in the case of using a curemeter to discriminate scorch differences between batches, a test must be run until it scorches, and, in order to be assured that scorch occurs, the test time must be long enough so that all batches scorch within the predetermined time. By design, this time is typically unnecessarily long for some of the batches. Likewise, when fully curing rubber batches, for a fixed time, for the purpose of analyzing after cure properties, the time must be long enough to ensure complete cure for all batches, as under cure or over cure will affect the after cure properties. Thus, tests for analyzing after cure properties are also typically unnecessarily long in order to ensure that full cure has been reached for all batches being tested. In the prior art, a good, discriminatory time/variable condition profile is determined only after running multiple experimental profiles with particular rubber batches and becoming familiar with them in order to determine if a particular time/variable condition profile correlates with the scorch and the full cure of the rubber batches. This general trial-and-error approach to determining test conditions, in addition to being burdensome and time consuming, may be inaccurate because differences between rubber batches might be such that a determined time/variable condition profile would call for changing the variable condition either too early or too late.

Thus, there is a need in the art for a method for testing the properties of a rubber sample wherein a test condition is varied, during testing, not according to experimentally predetermined time/variable condition profiles, but rather, according to the actual measured state of cure of the rubber sample itself. The need also exists for a method wherein each rubber batch variation is treated uniquely, according to the unique physical characteristics of that batch, during the vulcanization thereof. In particular, there exists a need in the art for a method for testing the properties of a rubber sample wherein the variable test condition is changed upon the scorch of the rubber sample being tested, and is additionally, or in the alternative, changed upon full cure of the rubber sample, wherein the time in which the variable test condition is changed is unique to each batch, thus saving time over the prior art where test conditions are not changed according to the characteristics of each individual rubber sample.

SUMMARY OF THE INVENTION

As used herein, "rubber" or "rubber sample" is to be understood to mean any vulcanizable polymeric material suitable for testing according to the method disclosed herein. These polymeric materials may include, by way of non-limiting example, elastomers, elastomeric compounds, thermoplastic elastomers, thermoset plastics, and the like. The types of polymeric materials suitable for testing according to this invention will be readily known to those of ordinary skill in the art.

As used herein, "state of cure" refers to the degree to which the rubber sample has been vulcanized or cured. The state of cure of a rubber sample can be generally quantified with reference to a measured physical property of the rubber sample, as, for example, with reference to measurements of torque or modulus. The state of cure of a rubber sample lies along the continuum from a completely uncured state to a completely cured state, and information regarding the state of cure of a given rubber sample can be obtained by analyzing a physical property of the rubber sample during the curing thereof.

In general, the present invention provides a process for testing the properties of a rubber sample wherein the rubber sample is subjected to a changing test condition. The process includes the steps of continuously measuring at least one physical property of the rubber sample to analyze the state of cure of the rubber sample; and adjusting the test condition when the state of cure is analyzed to satisfy a predetermined threshold.

In a more particular embodiment, this invention provides a process for testing the properties of a rubber sample comprising the steps of: contacting the rubber sample with a rotating or oscillating test instrument element; continuously measuring, as a function of time, a physical property of the rubber sample by analyzing the response of the rubber sample to the rotating or oscillating test instrument element, wherein the physical property is indicative of the state of cure of the rubber sample; setting a threshold for one or both states of cure selected from: (a) scorch of the rubber sample and (b) full cure of the rubber sample, wherein the threshold, whether for state (a) or (b), is based either upon a magnitude of the physical property measure in said step of continuously measuring or upon a calculated slope of the physical property as a function of time; and changing a test condition to which the rubber sample is subjected, when the threshold is found to be satisfied by the physical property measured in said step of continuously measuring, wherein the test condition is selected from temperature, degree of strain, frequency of oscillation, and combinations thereof.

PREFERRED EMBODIMENT FOR CARRYING OUT THE INVENTION

The method of this invention is based upon the continuous measurement and analysis of the state of cure of a rubber sample. To measure the state of cure of a rubber sample, any physical property of the rubber that is representative of the extent of curing of the rubber may be evaluated. Most commonly, the torque or modulus of the rubber sample would be measured as being relevant to the state of cure of the sample. Rheometers, curemeters, viscometers, and plastometers may be employed to test these properties, and the data obtained from these instruments may be plotted to provide a vulcanization curve, as is generally know.

Figure 1:
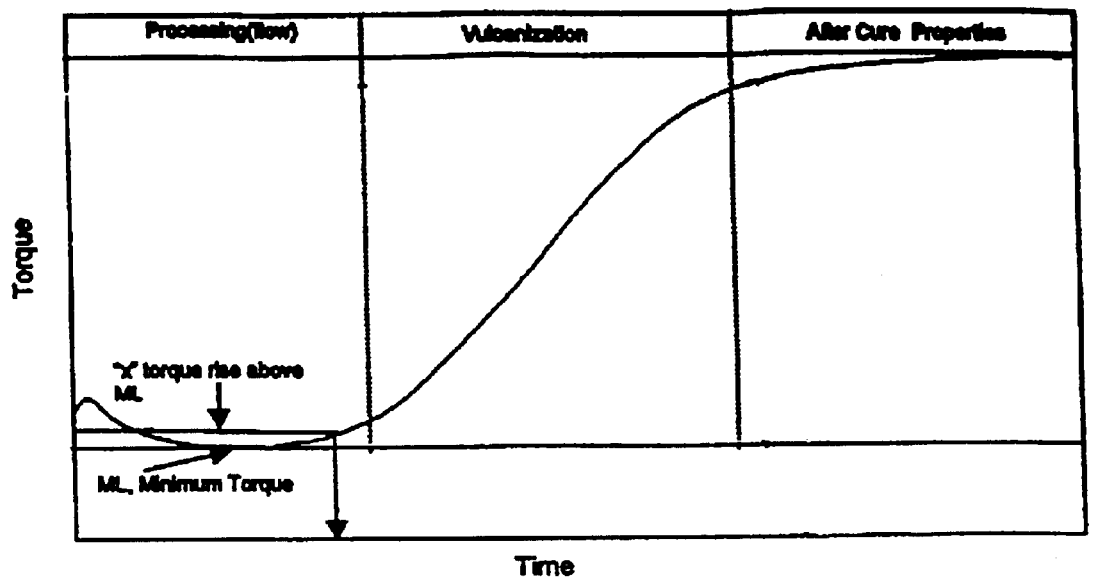
FIG. 1 provides a typical vulcanization curve showing torque as a function of test time and identifying critical points along the curve relating to scorch and full cure times and processing, vulcanization, and after cure stages.

Referring now to FIG. 1, a typical vulcanization curve is provided. This curve is based upon a measurement of torque, as a function of time, as the rubber sample changes from a flowing, processable, non-vulcanized rubber to a fully cured, more rigid rubber. As is generally known, the torque is measured as a resistance to the rotation (or oscillation) of a rotor, die, disc, or similar instrument element (herein "rotor") that is in contact with the rubber sample during the vulcanization thereof. As vulcanization progresses, the rubber becomes more rigid, and greater torque is needed to turn the rotor against the rubber sample.

As mentioned, in order to better quantify the processability of a rubber sample, it is generally desirable to measure the properties of the sample at one or more temperatures, strains, and/or frequencies. Thus, the temperature of the rubber sample and/or the frequency at which the rotor oscillates and/or the degree of oscillation might be varied during vulcanization.

In the prior art, changes in a test condition are made according to predetermined time/variable condition profiles that are generally experimentally determined for different rubber batches. In this invention, continuous measurements are used to make determinations as to when to change a variable test condition during the testing of a rubber sample. More particularly, continuous measurements of physical data relating to the state of cure of the rubber sample are made and analyzed, and changes in the desired test condition are made according to the state of cure of the rubber sample as based upon the measured data. A "scorch threshold," based upon a measured physical property, will be used to signal the point at which the variable test condition may be changed for analyzing vulcanization properties or speeding up the time for reaching full cure (typically by a step or ramp change in temperature). Likewise, a "cure threshold," also based upon a measured physical property, will be employed to signal the point at which the variable test condition may be changed for the purpose of analyzing after-cure properties. In the method of this invention, each rubber batch can be treated uniquely, and, rather than employing experimentally determined time/variable condition profiles in an attempt to change a variable test condition as the rubber sample scotches, and, thereafter, again changing the test condition as the rubber sample reaches full cure, determinations of when to change the variable test condition can be made as the test itself progresses. Furthermore, through appropriate software, current testing equipment can be adapted to make these determinations and test condition changes automatically, without the aid of the operator of the testing equipment.

The "scorch threshold" may be based upon the physical property measured, either according to a unit rise above a minimum measured for that physical property or upon a change in slope of the physical property measured as a function of time. The "cure threshold" may be based upon the physical property measured, according to the slope of the change in the physical property measured as a function of time. Most typically, the physical property being measured would be elastic torque; however, it may also be complex dynamic torque, loss torque, tan delta or the equivalent modulus values calculated from the torque values. Indeed, any physical property that is representative of the state of cure of a rubber sample many constitute the measured physical property.

The thresholds discussed above are based upon an understanding of a typical vulcanization curve. Referring again to FIG. 1, it can be seen that the exemplary vulcanization curve shown therein is based upon measuring torque as a function of time as the rubber sample progresses from a processable, non-cured, flowing state to a completely cured state. As mentioned, the equipment employed will typically be a curemeter or similar device that is capable of measuring physical properties, such as elastic torque, as the rubber sample is vulcanized. In the vulcanization curve of FIG. 1, as the rubber sample is initially processable and able to flow, there is a decrease in torque due to the physical manipulation of the rubber sample by the oscillating (or rotating) rotor of the curemeter. The measured torque reaches a minimum, as indicated in FIG. 1 at ML, and, as the rubber sample vulcanizes, the slope of the vulcanization curve increases. The slope of the vulcanization curve continues to increase during vulcanization, until the rubber sample begins to approach full cure, at which time the slope once again begins to decrease, approaching a maximum torque asymptote. Based upon this understanding of state of cure data, application of the "scorch threshold" and "cure threshold" is explained below.

In the method herein, appropriate software and computers or microprocessors are employed to continuously evaluate the measured physical property, particularly with respect to changes in the physical property over time (i.e., the slope of the vulcanization curve data). This evaluation is described with reference to FIG. 2. Therein it is seen, as in FIG. 1, that the slope of the vulcanization curve changes as the rubber sample is vulcanized. Before vulcanization occurs, the slope, S1, is close to zero. As vulcanization progresses, the slope increases, as illustrated by slopes S2 and S3. As cure reaches completion, the slope decreases and again begins to approach zero, as shown by slopes S4 and S5. The software and hardware employed would use two or more points (preferably very close in time, approaching a time difference of 0) along the vulcanization curve to calculate the slope of the curve, and, based upon these continuous measurements, will decide when to change a variable test condition.

The scorch threshold may be based upon the physical property measured. Accordingly, a unit rise above the minimum physical property value, ML (FIG. 1) is used for this threshold. That is, once the software and computer/microprocessor associated with the testing equipment locates minimum ML, it records the value of the physical property at that minimum point, and thereafter, compares measured physical properties against that minimum value until the desired unit rise above minimum is met. This is visually represented in FIG. 1, wherein an "x" torque rise above ML is shown on the graph. When the physical property is elastic torque, the scorch rise threshold (x) above minimum (ML) will typically be set at between 1 or 2 dNm, as defined in ASTM D2084, or might be set at 1 dNm, as defined in ASTM D5289. This torque-based scorch threshold may be as low as 0.25 dNm or less, and sometimes as high as 5 dNm.

Figure 2:
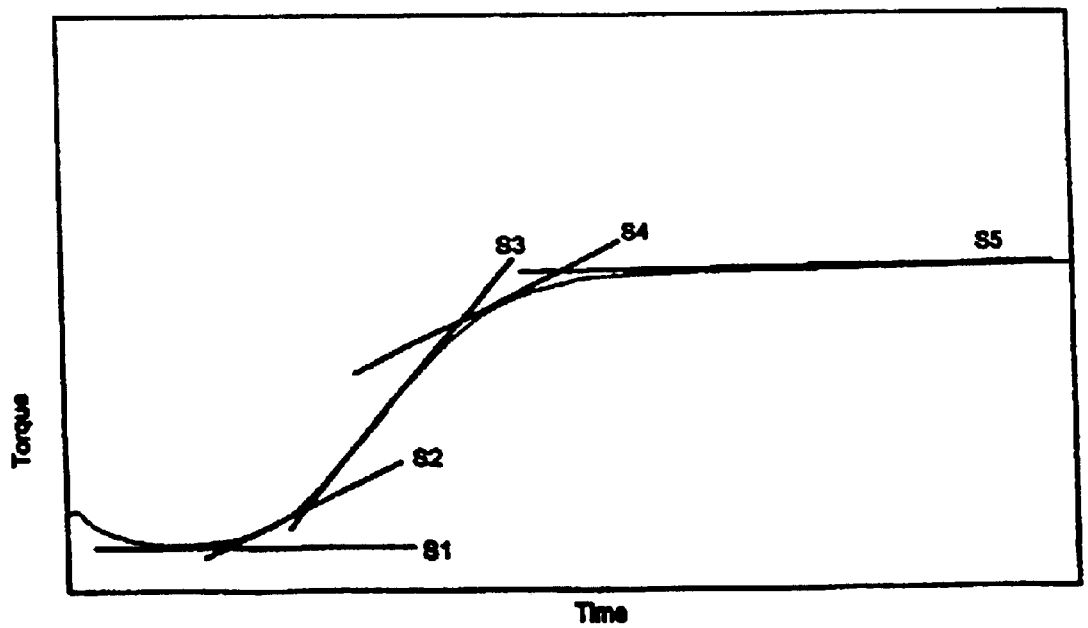
FIG. 2 generally depicts the changes in slope that occur in a typical vulcanization curve.

The scorch threshold may alternatively be based on the change in slope of the physical property measured as a function of time As noted and appreciated from FIGS. 1 and 2, the measured physical property (which is representative of the state of cure of the rubber sample) reaches a minimum before the onset of cure, i.e., before scorch, and the slope of the physical property as a function of time is negative up to this minimum. The change to positive slope indicates the onset of cure, and a positive slope value for the physical property versus time can thus serve as a scorch threshold. Most typically, this property is elastic torque. However, it may also be complex dynamic torque, loss torque, tan delta or the equivalent modulus values calculated from the torque values. When the property is elastic torque, the scorch slope threshold is typically set close to zero, and generally in the range of 0.1 to 2.0 dNmn/min.

The cure threshold is based on the change in slope of the physical property being measured as a function of time, which, most typically, is elastic torque. However, it may also be complex dynamic torque, loss torque, tan delta or the equivalent modulus values calculated from the torque values. The cure threshold, when based on elastic torque, is typically set close to zero and is in the range of zero to 1.0 dNm/min. For compounds with a marching modulus, this value may be even larger.

Notably, the test system employed must be able to distinguish between slope-based thresholds for scorch and cure, since both thresholds may approach zero. The system may determine the start of the measurement by continuously looking for a minimum value. When this is obtained, the slope will be close to zero. The slope values increase after this point. The first positive, non-zero slope that is obtained signifies the onset of cure (i.e., scorch). At this point or thereafter, the scorch threshold will be applied. The cure threshold is applied after the scorch threshold has been met. That is, after the first positive, non-zero slope is calculated, measurements of the physical property under consideration are compared against the unit rise-based or slope-based scorch thresholds, and, once the scorch threshold is met, and, if desired, a test condition is changed, the system switches to compare the measured physical property to the slope-based cure threshold.

The scorch and cure thresholds are signals to perform a test condition change in the cure meter. The most common condition change would be temperature, but temperature, frequency of oscillation, or degree of oscillation may be changed either individually or in combination.

In the most common application of the process taught herein, a test would be started at a relatively low temperature, e.g. 100° C. This temperature may be as high as 160° C., but is generally less than the vulcanization temperature. When the scorch threshold is met, a signal is sent to the curemeter to change the temperature. This is generally a temperature increase to the vulcanization temperature. Typical vulcanization temperatures are greater than 150° C. and are more often in the range of 160 to 200° C.

A second application of the scorch threshold is to test a sample at either a high frequency or a large strain to measure flow and scorch characteristics prior to vulcanization. When the scorch threshold is met, the strain and/or frequency would be changed and would typically be reduced. The temperature could also be changed as described in the above paragraph. In many cases this would be a temperature increase to a temperature associated with vulcanization. Strains may be selected in the range of from 1 to 150% or greater, and frequencies selected in the range of 0.1 to 30 Hz although this invention is not limited thereto or thereby.

The cure threshold would most commonly be used to change a temperature at the end of an isothermal cure. This temperature change would generally be a temperature decrease. The vulcanization temperature would be as described above (i.e., 150° C., typically from about 160° to about 200° C.). The temperature after the cure threshold is met is generally in the range from about 40° to about 100° C. and typically about 60° C. This temperature may vary greatly depending on the capabilities of the equipment (e.g., curemeter) and the desired application temperature. After the temperature decreases, the cured dynamic properties could be measured as required by ASTM D6601.

The cure threshold could also be used to signal a change in frequency or strain of the test. This would typically be to increase strains or frequencies after the cure threshold is met. The strains would be in the range of from about 1% to about 50% and even higher, and frequencies would be in the range of from about 0.1 to about 35 Hz. This recitation of particular ranges of strains and frequencies is not to limit the present invention.

In light of the foregoing, it should thus be evident that the present invention, providing a process for testing the properties of a rubber sample, substantially improves the art. While, in accordance with the patent statutes, only the preferred embodiments of the present invention have been described in detail herein above, the present invention is not to be limited thereto or thereby. Rather, the scope of the invention shall include all modifications and variations that fall within the scope of the attached claims.

What is claimed is:

1. A process for testing the properties of a rubber sample wherein the rubber sample is subjected to a changing test condition comprising:
    continuously measuring at least one physical property of the rubber sample to analyze the state of cure of the rubber sample;
    adjusting the test condition when the state of cure is analyzed to satisfy a predetermined threshold; and
    continuing the testing process.

2. The process of claim 1, wherein the physical property of said step of continuously measuring at least one physical property is selected from torque, modulus, and tangent delta.

3. The process of claim 2, further comprising the step of determining a minimum physical property value, ML, that is the minimum value of the at least one physical property of the rubber sample that is being measured in said step of continuously measuring, wherein the predetermined threshold is a predetermined value, above ML, of the at least one physical property measured in said step of continuously measuring.

4. The process of claim 3, wherein the physical property is torque, ML is a minimum torque value, and the predetermined threshold is a predetermined torque value above ML.

5. The process of claim 4, wherein the predetermined torque value is from about 0.25 to about 5 dNm above the minimum torque value.

6. The process of claim 1, wherein said step of continuously measuring the state of cure of the rubber sample includes continuously analyzing data relating to the slope of a curve of the at least one physical property of the rubber sample as a function of time.

7. The process of claim 6, wherein the predetermined threshold is a predetermined slope value for data relating to the curve of the physical property as a function of time.

8. The process of claim 7, wherein the physical property is torque, and the predetermined threshold is a predetermined slope value for torque as a function of time.

9. The process of claim 8, wherein the predetermined slope value is from about 0.1 dNm/min to about 2.0 dNm/min.

10. The process of claim 1, wherein the test condition that is adjusted in said step of adjusting the test condition is selected from temperature, degree of strain, frequency of oscillation, and combinations thereof.

11. A process for testing the properties of a rubber sample comprising the steps of:
    contacting the rubber sample with a rotating or oscillating test instrument element;
    continuously measuring, as a function of time, a physical property of the rubber sample by analyzing the response of the rubber sample to the rotating or oscillating test instrument element, wherein the physical property is indicative of the state of cure of the rubber sample;
    setting a threshold for one or both states of cure selected from:
        (a) scorch of the rubber sample and
        (b) full cure of the rubber sample, wherein the threshold is based upon a magnitude of the physical property measure in said step of continuously measuring or upon a calculated slope of the physical property as a function of time;
    changing a test condition to which the rubber sample is subjected, when the threshold is found to be satisfied by the physical property measured in said step of continuously measuring, wherein the test condition is selected from temperature, degree of strain, frequency of oscillation, and combinations thereof; and
    continuing the testing process.

12. The process of claim 11, further comprising the step of determining a minimum physical property value, ML, that is the minimum value of the at least one physical property of the rubber sample that is being measured in said step of continuously measuring, wherein the predetermined threshold is a determined value, above ML, of the at least one physical property measured in said step of continuously measuring.

* * * * *